US010604445B2

(12) United States Patent
Jose et al.

(10) Patent No.: US 10,604,445 B2
(45) Date of Patent: Mar. 31, 2020

(54) PROCESS FOR ION IMPLANTATION

(71) Applicant: UNIVERSITY OF LEEDS, Leeds, Yorkshire (GB)

(72) Inventors: Gin Jose, Leeds (GB); Toney Teddy Fernandez, Kerala (IN); Peter John Grant, Leeds (GB); Animesh Jha, Leeds (GB); Sikha Saha, Leeds (GB); David Paul Steenson, Bradford (GB)

(73) Assignee: UNIVERSITY OF LEEDS, Leeds (GB)

( * ) Notice: Subject to any disclaimer, the term of this patent is extended or adjusted under 35 U.S.C. 154(b) by 697 days.

(21) Appl. No.: 14/377,403

(22) PCT Filed: Feb. 8, 2013

(86) PCT No.: PCT/GB2013/050300
§ 371 (c)(1),
(2) Date: Aug. 7, 2014

(87) PCT Pub. No.: WO2013/117941
PCT Pub. Date: Aug. 15, 2013

(65) Prior Publication Data
US 2015/0353419 A1  Dec. 10, 2015
US 2017/0152174 A9  Jun. 1, 2017
US 2017/0297958 A9  Oct. 19, 2017

(30) Foreign Application Priority Data

Feb. 8, 2012  (GB) .................................. 1202128.3

(51) Int. Cl.
C23C 14/32  (2006.01)
C03C 23/00  (2006.01)
(Continued)

(52) U.S. Cl.
CPC ........ *C03C 23/0055* (2013.01); *A61B 5/1455* (2013.01); *C03C 3/04* (2013.01);
(Continued)

(58) Field of Classification Search
CPC ....... C23C 14/221; C23C 14/28; C23C 14/32; C23C 14/48; C03C 23/005; B05D 3/06; B05D 3/144; B05D 3/148
(Continued)

(56) References Cited

U.S. PATENT DOCUMENTS 4,281,030 A * 7/1981 Silfvast ................ C23C 14/022
427/566
4,714,628 A * 12/1987 Eloy ....................... C23C 14/28
427/523
(Continued)

FOREIGN PATENT DOCUMENTS

CN  101186446  5/2008
DE  19756348  4/1999
(Continued)

OTHER PUBLICATIONS

G. Jose et al.; "High Quality Erbium doped Tellurite Glass Films Using Ultrafast Laser Deposition"; ICTON 2009 We.B5.4 ; 978-1-4244-4826-5/09/IEEE; 4 pages; 2009 (no month).*
(Continued)

*Primary Examiner* — Marianne L Padgett
(74) *Attorney, Agent, or Firm* — Niels Haun; Dann, Dorfman, Herrell & Skillman, P.C.

(57) ABSTRACT

The present invention relates to a substrate comprising an ion-implanted layer, for example a cation, wherein the ion implanted layer has a substantially uniform distribution of the implanted ions at a significantly greater depth than previously possible, to a well-defined and sharp boundary within the substrate. The invention further comprises said
(Continued)

sub-strate wherein the substrate is a silicon based substrate, such as glass. The invention also comprises the use of said material as a waveguide and the use of said material in measurement devices.

10 Claims, 12 Drawing Sheets

(51) Int. Cl.
| | |
|---|---|
| *C03C 3/04* | (2006.01) |
| *C23C 14/48* | (2006.01) |
| *A61B 5/1455* | (2006.01) |
| *C23C 14/28* | (2006.01) |
| *C23C 14/22* | (2006.01) |
| *G02B 6/12* | (2006.01) |

(52) U.S. Cl.
CPC ............ *C23C 14/221* (2013.01); *C23C 14/28* (2013.01); *C23C 14/32* (2013.01); *C23C 14/48* (2013.01); *G02B 2006/12061* (2013.01); *G02B 2006/12188* (2013.01); *Y10T 428/31* (2015.01); *Y10T 428/315* (2015.01)

(58) Field of Classification Search
USPC ....... 427/525, 526, 527, 529, 528, 530, 531, 427/572, 561, 596, 597, 162, 164, 165
See application file for complete search history.

(56) References Cited

U.S. PATENT DOCUMENTS

| | | | |
|---|---|---|---|
| 5,342,690 A | | 8/1994 | Platts |
| 5,760,362 A | * | 6/1998 | Eloy ...................... A61B 18/26 118/623 |
| 5,763,340 A | | 6/1998 | Nishii et al. |
| 5,871,826 A | * | 2/1999 | Mei .......................... H01L 21/22 257/E21.134 |
| 6,019,796 A | * | 2/2000 | Mei ....................... H01L 21/223 257/E21.141 |
| 6,372,585 B1 | | 4/2002 | Yu |
| 6,509,070 B1 | * | 1/2003 | Voevodin .............. C23C 14/083 427/458 |
| 10,435,567 B2 | * | 10/2019 | Slagter ................... C09D 5/006 |
| 2006/0243321 A1 | * | 11/2006 | Yamada ................. B01J 35/004 136/263 |
| 2009/0012523 A1 | * | 1/2009 | Ruuttu ................ A61F 2/30767 606/76 |
| 2012/0225220 A1 | * | 9/2012 | Jose ...................... H01S 3/0632 427/596 |
| 2013/0011440 A1 | * | 1/2013 | Herbst ..................... A61L 27/30 424/400 |
| 2014/0227461 A1 | | 8/2014 | Darwish |
| 2015/0132507 A1 | * | 5/2015 | Jose ........................ B23K 26/38 427/596 |
| 2019/0256413 A1 | * | 8/2019 | Jose ..................... A61B 5/1455 |

FOREIGN PATENT DOCUMENTS

| | | |
|---|---|---|
| EP | 0318440 | 5/1989 |
| GB | 2080027 | 1/1982 |
| JP | 08133793 | 5/1996 |
| JP | 2005219944 | 8/2005 |
| JP | 2010184825 | 8/2010 |
| WO | 2005048831 | 6/2005 |
| WO | 2005080285 | 9/2005 |
| WO | 2011030157 | 3/2011 |
| WO | 2013117941 | 8/2013 |

OTHER PUBLICATIONS

G. Jose et al. "Ultrafast Laser Deposition of Oxide Glass Film"; 978-1-4244-4080-1/09/IEEE; 2009 (no month); a single page.*
S.Shen et al.; "Fabrication of Er3+ doped oxychloride-silicate glass film by pulsed laser deposition for planar amplifier"; Journal of Non-Crystalline Solids; vol. 355; 2009 (available online Aug. 31, 2009); pp. 1893-1896.*
Webster's Ninth New Collegiate Dictionary; Merriam-Webster inc. ;Springfield, Massachusetts, USA; 1990 (no month); excerpt p. 733.*
Julius Grant, editor; Hackh's Chemical Dictionary, 3rd edition; McGraw-Pill Book Company, inc.; New York; 1944 (no month); excerpt p. 518.*
Richard J Lewis, Sr., editor; Hawley's Condensed Chemical Dictionary, 12th edition; Van Nostrand Reinhold Company, New York; 1993 (no month), excerpt p. 563.*
Amerov, A., et al., "Molar Absorptivities of Glucose and Other Biologial Molecules in Aqueous Solutions Over the First Overtone and Combination Regions of the Near-Infrared Spectrum", Applied Spectroscopy, vol. 58, No. 10, 2004, 1195-1204.
Amerov, A., et al., "Scattering and Absorption Effects in the Determination of Glucose in Whole Blood by Near-Infrared Spectroscopy", Analytical Chemistry, vol. 77, No. 14, Jul. 15, 2005, pp. 4587-4594.
Amerov, A., et al., "In Vitro Kromoscopic Analysis of Glucose in Blood", SPIE vol. 4965, 2003, pp. 7-16.
Goldstein, D., et al., "Glycated Hemoglobin: Methodoligies and Clinical Applications", Clinical Chemistry, vol. 32, No. 1(b), 1986, pp. B64-B70.
Mazarevica, G., et al., "Properties of Erythrocyte Light Refraction in Diabetic Patients", Journal of Biomedical Optics, Apr. 2002, vol. 7, No. 2, pp. 244-247.
Maier, J., et al., "Possible Correlation Between Blood Glucose Conentration and the Reduced Scattering Coefficient of Tissues in the Near Infrared", Optics Letters, vol. 19, No. 24, Dec. 15, 1994, pp. 2062-2064.
Shvartsman, L., et al., "RBC Aggregation Effects on Light Scattering From Blood", SPIE vol. 4162, 2000, pp. 120-129.
Kohl, M., et al., "Influence of Glucose Concentration on Light Scattering in Tissue-Simulating Phantoms", Optics Letters, vol. 19, No. 24, Dec. 15, 1994, pp. 2170-2172.
Skelland, N., et al., "Ion Implantation Into Heated Soda-Lime Glass Substrates", Journal of Non-Crystalline Solids 188 (1995), pp. 243-253.
GB Search Report dated Jan. 18, 2013 corresponding to GB Application No. GB1202128.3.
International Search Report and Written Opinion dated Aug. 20, 2013 in corresponding international application No. PCT/GB2013/050300.
McCartney, et al., Near-Infrared Fluorescence Lifetime Assay for Serum Glucose Based on Allophycocyanin-Labeled Concanavalin A, Analytical Biochemistry 292, 216-221 (2001), Apr. 10, 2001.
Giuffrida et al., Surface ion implantation induced by laser-generated plasmas, Radiation Effects and Defects in Solids, 165:6-10, 534-542, Sep. 15, 2010.
"Standard Test Method for Assignment of the Glass Transition Temperatures by Differential Scanning Calorimetry1"; ASTM International; Designation: E 1356-03, May 2003.
Arun K. Varshneya ; "Fundamentals of Inorganic Glasses"; New York State College of Ceramics Alfred University Alfred, NY & Saxon Glass Technologies, Inc. Alfred, NY pp. 402-404, 2013.
Zoe H. Barber; "The control of thin film deposition and recent developments in oxide film growth"; Journal of Materials Chemistry; Sep. 20, 2005; pp. 334-344.

* cited by examiner

PROCESS FOR ION IMPLANTATION

RELATED APPLICATIONS

This application is a 371 application of International Application No. PCT/GB2013/050300 filed Feb. 8, 2013, which claims the benefit of priority of United Kingdom Patent Application No. 1202128.3 filed Feb. 8, 2012. Each of the foregoing applications is hereby incorporated herein by reference.

FIELD OF THE INVENTION

The present invention relates to a substrate comprising an ion-implanted layer, for example a cation, wherein the ion implanted layer has a uniform distribution of the implanted ions at a significantly greater depth than previously possible. The invention further comprises said substrate wherein the substrate is a silicon based substrate, such as glass. The invention may also comprise the use of said material as a waveguide and/or the use of said material in measurement devices.

BACKGROUND

Femtosecond pulsed laser plasma deposition (fs-PLD) is a relatively new technique compared to its nanosecond pulsed counterpart. Technologically realized in a solid-state device in mid 90s, the fs-PLD is currently emerging as one of the promising technology in the field of thin film deposition due to the employment of femtosecond lasers. Depending on the repetition rate and pulse duration in a fs laser-matter interaction can be tuned to become either a hot process with heat diffusion or, a cold process due to the lack of a heat diffusion process and hence, the laser is used for the production of plasma plume and energetic ions in several other techniques such as ion implantation. Recent reports in the fs-PLD thin films are mainly based on crystalline and semiconductor materials. At the present time implantation at a scale of only a few tens of nanometer, otherwise known as sub-plantation, have been reported. We have found that implantation to a much larger depth is possible. This observation has the potential to produce new materials and structures which are otherwise impossible to fabricate. The unique possibility of implanting ions, such as rare earth ions opens new realm of photonic devices engineering with respect to site selective doping by masking, direct printing of photonic circuits, integrated optical amplifiers in novel materials, multiple sensors with integrated pump source and data readouts, possibility of single chip multi-sensor design, superlattice structures by multi-target deposition.

International patent application, publication number: WO 2011/030157 describes a method of applying a film to a substrate by ablating a target with radiation from a laser whereby a quantity of the target layer is deposited on the substrate. Skelland and Townsend (1995) Journal of Non-Crystalline Solids 188, 243-253 describes ion-implantation into heated soda-lime glass substrates whereby the profile of the ions implanted shows a distinct peak with a gradual drop in ion density either side.

BRIEF SUMMARY OF THE DISCLOSURE

The applicants have found a process which enables an ion layer to be implanted into a substrate, such as glass to a much greater depth than previously possible.

Thus, according to a first aspect of the invention there is provided a substrate comprising an ion-implanted layer wherein the penetration depth of the implanted ions is at least 50 nm, or at least 200 nm, for example at least 500 nm.

The applicants have also found that the process provides a substantially uniform distribution density of the implanted ions in the implanted layer rather than the density profile showing a peak followed by a drop off in implanted ion density, in a manner which the ion depths transcend conventional diffusion and high-energy ion implantation, due to major structural barriers for ion diffusion/implantation. The applicants have also found that the process provides a very rapid and substantially discontinuous termination in the distribution density of the implanted ions at the terminal boundary of the implanted layer within the substrate, rather than the density profile showing a gradual and continuous drop-off in implanted ion density. The ion distribution, or concentration level, may fall from the average (e.g. substantially uniform) level of the layer to a substantially ion-free concentration level or distribution, over a distance of about 30 nm or less, or more preferably about 20 nm or less or yet more preferably about 10 nm or less. This enables a sharply-defined inner terminal "edge" to be formed in the implanted layer.

Thus, according to a further aspect of the invention there is provided a substrate comprising an ion-implanted layer wherein the ion implanted layer has a substantially uniform distribution of the implanted ions. Substantial uniformity may be along the transverse and horizontal sections/directions, both in the direction across the implanted substrate surface and transverse to it (i.e. into the surface). The substantial uniformity in the ion distribution may manifest itself as a substantially uniform implanted ion concentration level that varies by no more than +/−10% about the average ion concentration level of the layer as a whole, or more preferably by no more than +/−8%, or yet more preferably by no more than +/−5% about the average ion concentration level of the layer as a whole. This variation may be quantified in terms of a standard deviation value of the ion concentration level. It is postulated, but not asserted, that the uniformity in ion distribution may arise as follows. A target glass may be irradiated by a powerful pulsed laser, for example, to generate by laser ablation an ion cloud for implantation into the surface of a substrate to form a functional surface as described herein. An initial ablation pulse causes a first flux of ions to reach the substrate surface whereupon the ions are implanted substantially at the surface, rather than at significant depth. A subsequent laser ablation pulse generates a second flux of ions at the substrate surface, which displace the pre-implanted ions (the first ion flux) further into the substrate and in doing so substantially occupy the substrate surface region previously occupied by the first flux of ions. The process of inward displacement of all previously implanted ions in the substrate, by each successive influx of ions at the substrate surface, is thought to "stack-up" implanted ions ever further into the body of the substrate in a distribution extending (to below) its surface. The uniformity of the distribution may arise in part from the uniformity of the ablation laser light characteristics (light energy, light wavelength, ablating pulse duration, pulse repetition rate etc).

According to a further aspect of the invention, there is provided a substrate comprising an ion-implanted layer wherein the ion implanted layer extends substantially from the outermost surface of the substrate. The ion-implanted layer may have a substantially uniform distribution of the implanted ions extending into the substrate from its outermost surface. This differs from existing ion implanted layers which are formed by firing energetic ions into a substrate to form a buried layer existing some significant distance below the surface of the substrate. Ion implantation extending to the surface of the substrate has advantages including increased sensitivity in a biosensor of an aspect of the invention, and also the direct formation of surface optical structures such as regions of increased refractive index and/or waveguide structures in the substrate (e.g. a photonic circuit pattern).

We have also found that the process facilitates ion-implantation to a higher density than prior art processes.

Thus, according to a further aspect of the invention there is provided a substrate comprising an ion-implanted layer wherein the ion implanted layer has an implanted ion density of the order of 10,000 to several hundred thousands of ppm, depending on the concentrations of ions in the target material used for fs-laser ablation. For example, when a target of tellurite glass with 80 mol % $TeO_2$-10 mol % ZnO-9 mol % $Na_2O$ and 1 mol % $Er_2O_3$ oxide was used to make laser-plasma implantation on a clean silica surface at 700° C., the implanted ion concentrations of $Te^{4+}$, $Na^+$, $Zn^{2+}$, and $Er^{3+}$ correspond to nearly half of the cation concentrations in the bulk target materials (e.g. 50 ion % $Si^{4+}$, 40 ion % $Te^{4+}$, 5 ion % of $Zn^{2+}$, 4.5 ion % of $Na^+$, and 0.5 ion % of $Er^{3+}$). These densities are larger than $10^{21}$ ions $cm^{-3}$. In conventional processes, the achievable densities are an order magnitude less. This specific ability to achieve remarkably high ion concentrations permits us to engineer bespoke surfaces which have been unachievable in the past for light guiding applications. Such an approach also allows us to engineer the dielectric and spectroscopic properties in the implanted layer. For example, the implanted layer may be doped with rare-earth ions for engineering lasers and amplifiers, but also be vertically integrated with relevant mirrors and photo-active/sensitive materials, e.g. a metal, polymer, semiconductor, ferro-electric ceramic for frequency conversion and manipulation, a biological surface with a protein. A multitude of optically active and passive functions may be achievable via a combination of chemically dissimilar materials on to a dielectric surface (glass, polymer and ceramic).

According to a further aspect of the invention there is provided a substrate comprising an ion-implanted layer wherein
(i) the ion implanted layer has a substantially uniform distribution of the implanted ions;
(ii) wherein the penetration depth of the implanted ions is at least 50 nm or at least 200 nm, for example at least 500 nm.

According to a further aspect of the invention there is provided a substrate comprising an ion-implanted layer wherein
(i) the ion implanted layer has a substantially uniform distribution of the implanted ions; and
(ii) the implanted ion density is at least $10^{18}$ ions $cm^{-3}$ (e.g. $10^{21}$ ions $cm^{-3}$ or more, such as about $10^{23}$ ions $cm^{-3}$).

According to a further aspect of the invention there is provided a substrate comprising an ion-implanted layer wherein
(i) the penetration depth of the implanted ions is at least 50 nm or at least 200 nm, for example at least 500 nm; and
(ii) the implanted ion density is at least $10^{18}$ ions $cm^{-3}$ (e.g. $10^{21}$ ions $cm^{-3}$ or more, such as about $10^{23}$ ions $cm^{-3}$).

According to a further aspect of the invention there is provided a substrate comprising an ion-implanted layer wherein
(i) the ion implanted layer has a substantially uniform distribution of the implanted ions;
(ii) wherein the penetration depth of the implanted ions is at least 50 nm or at least 200 nm; and
(iii) the implanted ion density is at least $10^{18}$ ions $cm^{-3}$ (e.g. $10^{21}$ ions $cm^{-3}$ or more, such as about $10^{23}$ ions $cm^{-3}$).

The penetration depth of the ion layer depends on the substrate used but in general would be at least 50 nm or at least 250 nm, at least 300 nm, at least 400 nm, at least 500 nm, at least 750 nm, at least 1 µm, at least 1.5 µm, at least 2.0 µm, at least 2.5 µm and at least 3 µm. In one embodiment the layer has a depth from about 0 nm to about 3 µm, for example in the range about 0 nm to about 2.5 µm, about 0 nm to about 2 µm, about 0 nm to about 1.5 µm or about 0 nm to about 1 µm. In a further embodiment the layer has a depth from about 500 nm to about 3 µm, for example in the range about 500 nm to about 2.5 µm, about 500 nm to about 2 µm, about 500 nm to about 1.5 µm or about 500 nm to about 1 µm.

In general the implanted ion density may be at least $10^{18}$ ions $cm^{-3}$ may be up to $10^{23}$ ions $cm^{-3}$ (e.g. in silica glass), for example $5\times10^{21}$ ions $cm^{-3}$.

The ion implanted layer may comprise one or more different ions.

The implanted layer may be on an outside face of the substrate or may comprise a layer within the substrate. The implanted layer may comprise one layer or may comprise two or more layers with a distinct combination of ion compositions in each layer. For the avoidance of doubt where there are more than two layers, two or more non-adjacent layers may have the same ion composition, for example, to form a sandwich. Multiple dissimilar materials as targets can be envisaged for tailoring the ion layer composition. A first layer may be initially formed, extending from the surface of the substrate to a given depth, and a second layer may be subsequently formed either by adding further implanted ions to the implanted ions in the existing layer, or by pushing the ions of the existing layer to greater depth within the substrate thereby forming two adjacent and successive layers. For example, a first layer may be formed using ions of a first element (or group of elements) by a process of ion implantation according to the methods of the invention. Then, a second layer may be formed over the first layer using ions of a second element (or a second group of elements) different from the first group. It has been found that the implantation of the second ions at the surface previously implanted by the first ions, cases the layer of first ions to be pushed/displaced further into the substrate by the second ions. The result is an implanted layer extending from the surface of the substrate to a depth of the upper sub-layer of the second ions, and then extending from the edge of the upper sub-layer to a lower sub-layer comprising the first ions.

The implanted layer can encompass substantially the whole area of the substrate or can comprise one or more zones (e.g. optical waveguide path patterns). The zones may comprise distinct areas on or within the substrate or one or more of the zones may overlap. The zones may comprise the same ion or ions or one or more of the zones may comprise a different ion or ions.

The ion may be a cation.

The ion may be selected from any cation which is ionisable, for example one or more of the following groups:

(i) one or more pre- lanthanide and/or lanthanide ions;
(ii) erbium, ytterbium, neodymium, praseodymium, holmium, cerium, yttrium, samarium, europium, gadolinium, terbium, dysprosium or lutetium ions;
(iii) $Nd^{3+}$, $Yb^{3+}$, $Er^{3+}$, $Tm^{3+}$, $Pr^{3+}$, $Ho^{3+}$, $Sm^{3+}$, $Eu^{3+}$, $Tb^{3+}$ and $Ce^{3+}$, $La^{3+}$ ions;
(iv) tellurium, germanium, zinc, sodium and erbium ions;
(v) metallic ions: for example, Bi, W, Nb, Ta, Ti, Mo, Cr, Mn, Ga, In, Sn, Pb
(vi) one or more one or more actinide ions;
(vii) actinium, americium, berkelium, californium, curium, einsteinium, fermium, lawrencium, mendelevium, neptunium, nobelium, plutonium, protactinium, thorium and uranium,
(viii) one or more transition metals;
(ix) one or more cations selected from the groups (i) to (ix) above.
(x) One or more anions which may be of $F^-$, $Cl^-$, $Br^-$, I, and chalcogen ions (S and Se).

The silicon-based substrate may comprise silicon, glass, silicon oxide or silicon hydride, siloxane polymer.

In a further embodiment the silicon-based substrate is glass. Example of glass include: silica, silicate, phosphate, tellurite, tellurite derivatives, germanate, bismuthate, borates, acetates, halides, chalcogenides and solgel route glasses.

The polymeric substrate may comprise Poly(methyl methacrylate) (PMMA), polyvinyl alcohol (PVA), polyether ether ketone (PEEK), polyethylene terephthalate (PET), polyimide(PI), polypropylene (PP), and polytetrafluoroethylene (PTFE), Polydimethoxy Siloxane (PDMS).

Novel ion-implanted substrates of the invention have application in a number of technologies, for example, in communication, computer or display technology, solidstate lighting and in laser assemblies. The novel ion-implanted substrate of the invention may be used in integrated optics (eg as a signal source, amplifier, wavelength splitter etc), chemical sensing, environmental sensing, biosensing, micro-nano spectroscopy, optical communication, micro fluidic devices, optofluidic devices, terahertz amplifiers, lab-on-chip or optical tomography.

The novel ion-implanted substrate of the invention may be used as a waveguide.

In one embodiment of the invention there is provided a waveguide comprising a ion-implanted substrate of the invention. Examples of optical waveguides include: slab waveguides, planar waveguides, optical fibres and other waveguides such as would be apparent to the skilled person.

The wavelength range of fluorescence in a chip comprising a substrate of the invention is governed by the ion which are implanted into the substrate. The skilled man would be familiar with the spectral properties of suitable doping ions and therefore chose the appropriate ions for preparing a ion-implanted substrate with suitable spectral properties.

| Example of the spectral properties include" | | |
|---|---|---|
| (i) | 950-1200 nm | $Yb^{3+}$; |
| (ii) | 1500-1650 nm range | $Er^{3+}$; |
| (iii) | 1400-1530 and 1600-2200 | Thulium; |
| (iv) | 1900-2500 nm | $Ho^{3+}$; |
| (v) | 1750 nm-2200 nm | codoping with $Tm^{3+}$ and $Ho^{3+}$ ions; |
| (vi) | 950 nm-2500 nm | codoping with $Yb^{3+}$, $Er^{3+}$, $Tm^{3+}$ and $Ho^{3+}$; |
| (vii) | 2000-4500 nm | $Dy^{3+}/Tb^{3+}/Er^{3+}$ |

A biosensor system according to an aspect of the invention may comprise:
(i) a laser (e.g. a pump laser);
(ii) an ion-implanted substrate of the invention (e.g. a waveguide with a functional surface); and
(iii) a light detector (e.g. for detecting light from the ion-implanted substrate).

A biosensor system according to an aspect of the invention may comprise:
(i) a laser (e.g. a pump laser);
(ii) an ion-implanted substrate of the invention (e.g. comprised in a photonic chip); and
(iii) a light detector and a signal processor for receiving and processing detection signals from the light detector (e.g. a photonic chip integrator).

The substrate may have a thickness in the range of about 0.1 mm to about 10 mm, such as in the range of 0.5 mm to about 3 mm, e.g. when used in waveguides of the invention. The substrate may be a thin layer (e.g. with a thickness of about 50 nm or more) of one or more of the following materials arranged or formed upon on any solid material e.g. a support material: silica, silicate, phosphate, tellurite, tellurite derivatives, germanate, bismuthate, borates, acetates, halides, chalcogenides and solgel route glasses. The laser may be arranged to input light at an end, side or edge of the substrate (e.g. waveguide) such that the laser light is guided along the substrate internally to the ion implanted substrate.

In one embodiment the detector is a fast photodiode. In one embodiment the photodiode is a microsecond photodiode, in a further embodiment a nanosecond photodiode.

One use of ion-implanted substrates of the invention is in the non-invasive detection of metabolites, such as glucose, in animals, such as in a novel method which measures photoluminescence lifetime.

In this method the photoluminescence spectral band of the dopant(s) overlaps with the characteristic absorption bands in the 1530-2200 nm) of the glucose molecules in the NIR wavelengths. The measured photoluminescence lifetime of the rare earth ions gets modified in the glass thin film contained in a photonic sensor due to the amplification by random scattering and localization of photoluminescent photons. When a medium containing glucose interacts with the film, the lifetime modifies as a function of glucose concentration due to its specific absorption as well as molecular scattering properties. Thus by an accurate measurement of the photoluminescence lifetime the concentration of glucose in the medium can be deduced. Since the absorption and scattering properties of the photons at different wavelengths within the emission band varies glucose concentration, the change in the photoluminescence lifetime at different wavelengths can be used as an additional feature to enhance the signal due to glucose from other interferences. This new measurement concept is named as Spectrally Resolved Photoluminescence Lifetime (SRPL) technique and is the novel principle of detection that is applied in the photonic sensor. This new approach avoids the disadvantages of direct spectroscopic methods such as low sensitivity due to strong signal absorption and provides capabilities of continuous glucose monitoring.

To describe the principle of the sensor based on photoluminescent lifetime measurement, the photonic chip and skin can be treated as a combined scattering medium because of their characteristically similar scattering properties. While the skin acts as scattering and absorption medium, gain or amplification of the optical signal is mainly provided by the doped functional surface which is under laser (980 nm) excitation/pumping.

Glucose molecules can interact with the NIR photons generated from the chip in two ways—namely, by absorption and by induced scattering. There is a strong dependency between the scattering properties of whole blood and the concentration of glucose matrix (e.g. ref. [1] below). A successful model was proposed based on several experimental observations leading to a possible explanation with scattering of light depending on the concentration of glucose in the blood and is likely caused by changes in the refractive index mismatch between RBC and plasma (see refs. [2, 3] below). Since it is observed that an increase in glucose concentration induce an increase in light scattering, it demands a large difference in the refractive index mismatch of red blood cells (RBC) and plasma. The refractive index of the RBC is known to be higher than the blood plasma and it is also quantified that the increase of refractive index of plasma with glucose addition is approximately $2.73 \times 10^{-5}$ per millimolar increase in glucose concentration (see refs [4, 5] below). If so, then the index of refraction of RBC should increase more to maintain a higher mismatch. The key reason behind the substantial increase in refractive index of RBC is thought to be due to the non-enzymatic glycation of the free amino groups of haemoglobin (see ref. [6]). However, there are refractive index variations due to the changes in the dimensions of the RBC leading to its increased packing density. These variations again depend upon the glucose uptake of the red blood cells, where it has been demonstrated that RBCs reduce their total diameter due to the osmotic shrinkage mechanism (reducing glucose concentration) and leads to an increase in light attenuation by the blood sample(see ref. [7]).

Any measured increase in the lifetime of the signal photons may be attributed to it being travelled longer paths in the medium as a result of increased probability of coherent scattering. This observation has been theoretically modelled whereby it can be demonstrated that the effective aqueous path length increased to between 1.1 and 1.2 mm compared to the 1 mm geometric path length of the sample cells used for the experiment (see ref. [1]). In a simple description, this means that the coherent scattering leads to longer measured/apparent lifetime while absorption by molecules reduces the apparent lifetime of the measured signal. Two distinct zones were observed in FIG. 7 where the fluorescence life time was measured against different glucose concentrations in human whole blood. It is postulated, but not asserted, that the reduction in fluorescence lifetime to about 400 μs at 10 mM glucose concentration could arise from absorption and/or incoherent scattering within the blood samples. But for concentrations above 10 mM, the lifetime was found to be increasing which can be attributed to coherent scattering process. This observation is consistent with the detailed explanation provided above regarding the refractive index mismatch between the plasma and red blood cells.

In addition, by the SRPL measurement method of an aspect of the invention, one may deduce the concentration of the molecule in question compared to other molecules (metabolites) and scatterers with interfering signals which are present, based on the wavelength dependent absorption coefficients. This may be relevant to non-invasive continuous glucose measurement as several interfering signals from the subject's skin may contribute to ambiguities in the measurements.

REFERENCES

[ref. 1] Airat K. Amerov et at., Analytical Chemistry 77 (14), 4587 (2005).
[ref. 2] G. Mazarevica et al., J Biomed Opt 7 (2), 244 (2002).
[ref. 3] Leonid D. Shvartsman et al., SPIE, Amsterdam, Netherlands, 2000 Vol. 4162, pp. 120.
[ref. 4] Matthias Kohl et al., Opt. Lett. 19 (24), 2170 (1994).
[ref. 5] John S. Maier et al., Opt. Lett. 19 (24), 2062 (1994).
[ref. 6] D. E. Goldstein et al., Clin Chem 32 (10 Suppl), B64 (1986).
[ref. 7] Airat K. Amerov et al., SPIE, San Jose, Calif., U.S.A., 2003 Vol. 4965, pp. 7.

FIG. 7 demonstrate this trend slope up to a concentration of ~10 mMol/L for three different wavelengths (1543 nm, 1550 nm, 1580 nm) when a ~1 μm thick $Er^{3+}$ implanted film was used for measurement in blood samples under controlled conditions. At concentrations higher than this however the trend reverses and it can attributed increasing competition between scattering and absorption. Glucose has a flat absorption response ($\sim 7 \times 10^{-5}$ $mM^{-1}mm^{-1}$) within 1534-1580 nm region, therefore at longer wavelengths the reduction in the scattering cross-section will be at a higher magnitude due to the $4^{th}$ power dependence of $\lambda$. At this context, the light photon-liquid medium interaction operates mainly on the absorption phenomenon where photons are lost leading to PL lifetime reduction. This phenomenon generally manifests in large increase (100's of microseconds) measured lifetime in the hypoglycaemic region and even up to concentration levels of 10 mMol/l and therefore results in excellent sensitivity.

In one embodiment of the invention there is provided a method for the non-invasive measurement of a metabolite in an animal which comprises:
  (i) applying a sensor on or near said animal, for example apply said sensor to the skin of the animal, said sensor comprising a functional surface (e.g in a waveguide) of the invention;
  (ii) irradiating said functional surface with a light source, for example, a laser, such that a portion of photoluminescence light escapes into the animal;
  (iii) measuring the photoluminescence lifetime of the escaped light wherein the recovery lifetime is correlated with the level of the metabolite.

In a further embodiment the change in the photoluminescence lifetime at different wavelengths can be used as an additional feature to enhance the signal due to a metabolite of interest from other interferences and also for calibrating the system.

A laser suitable for use in biosensor systems and detection methods of the invention include a laser in the visible and near infra red spectrum. For example, a laser with wavelengths in the near infra red spectrum such as those with wavelengths from about 780 to about 2200 nm, such as in the range about 980 nm to about 1100 nm, for example about 980 nm.

In one embodiment the power of said laser is in the range 1 mW to 500 mW, such as about 50 mW.

The light source, for example, a laser can have an angle of incidence at the substrate of 0° to 90°, for example, about 45°.

When measuring the recovery lifetime in detection methods of the invention the light source, for example, a laser is turned on an off, for example with a frequency of about 1 Hz to about 1000 Hz, or about 1 Hz to about 100 Hz, or about 1 Hz to about 10 Hz.

The detection technology of the invention provides wide detection bandwidth, for example, ranging from 800 to 4000 nm.

Waveguides or optical substrates suitable for methods of non-invasive measurement of the invention may comprise ion-implanted substrates of the invention, but would also include any waveguide or substrate which facilitates transmission of light and retrieval of a portion of said light from a biological material sufficient to measure the recovery lifetime. In one embodiment the functional surface is pumped by a tunable continuous wave (cw) laser within the range of about 1510 to about 1620 nm.

Metabolites which can be detected by the method of the invention include: small molecule metabolites, peptides, lipids, peptides, polypeptides and proteins. Myoglobin, HbA1C, Troponin and other substances may be detected.

Small molecules metabolites include: glucose and lactate.

The photoluminescence spectral band of the dopant(s) overlaps with the characteristic absorption bands of the metabolite or metabolites of interest. For example, in the case of detection of glucose a spectral band of about 1530 to about 2200 nm) of the glucose molecules would be acceptable.

In a further embodiment of the invention there is provided a process for making a ion-implanted substrate of the invention comprising:

ablating a target layer with incident radiation from an ultrafast laser in the presence of a substrate whereby to implant a quantity of the target layer in the substrate.

The process may further comprise employing one or more masks/stencils to facilitate implantation of ions in specific zones of the substrate.

The target layer can be any material which when exposed to incident radiation produces a plasma comprising ions capable of implanting into the substrate. Examples of target layers include tellurium-based glass.

In one embodiment the target layer is mounted on a rotational platform.

The substrate is spaced apart from the target layer, for example at a distance in the range about 0 mm to 150 mm, or about 50 mm to 150 mm, for example a distance of about 70 mm.

The substrate may be heated to facilitate the implantation of ions into the substrate. The optimum temperature to facilitate the implantation of ions will depend on the target material used. In general the optimum temperature is between 0.5 and 0.75 times the glass transition temperature. In embodiment, when using silica glass a temperature of about 973K can be used.

For example, the silica glass transition temperature is 1100-1200° C. Therefore the optimum range is about 550° C.-900° C. (823K-1173K).

The ultrafast laser may be a attosecond, femtosecond or picosecond laser. In one embodiment the ultrafast laser is a femtosecond laser.

The ultrafast laser may be, for example, a Ti-sapphire laser, a diode pumped laser such as a Yb-doped or Cr-doped crystal laser or a fibre laser.

The laser may be an excimer laser or an exciplex laser.

The laser may be an ultrafast pulsed laser.

In the process of the invention, the ultrafast laser may emit pulses of 15 ps or less for example pulses in the range 1 fs to 15 ps. In one embodiment in the process of the invention the ultrafast laser emits pulses of 150 fs or less, for example in the range about 50 to about 150 fs, for example about 100 fs.

The pulses may be emitted with a repetition rate in the range about 400 Hz to about 1 kHz. In one embodiment 400 Hz to 800 kHz, for example about 500 kHz.

The ultrafast laser may be mode-locked.

The average power of the ultrafast laser may be 80 W or less.

The pulse energy is typically in the range about 10 to 400 microjoules, or preferably about 10 to 200 microjoules, or more preferably about 40 to 150 microjoules, or yet more preferably about 40 to about 80 microjoules, for example about 50 to about 70 microjoules, such as about 65 microjoules.

Pulse energy may be selectively adjusted using an attenuator.

In one embodiment wavelength is typically about 800 nm, although a wide range of wavelengths would be suitable.

The incident radiation may be incident on the target glass at an angle in the range about 0° to about 80°, or about 40° to about 80°, for example about 60°.

The process is typically carried out in a vacuum chamber. The process may be carried out at reduced pressure, for example at a partial pressure of about 60 mTorr, or more preferably about 80 m Torr, or within the range of about 50 mTorr to about 90 m Torr.

The process may be conducted for example in the presence of a gas, such as oxygen or in an inert gas.

The duration of the process may be about 1 minute or more, for example about 30 minutes to about 10 hours, such as about 2 hours to about 8 hours. In one embodiment the duration is about 6 hours.

In a further embodiment of the invention there is provided a process for making an ion-implanted substrate of the invention comprising:

(i) providing a target layer;
(ii) providing a substrate in proximity to said target layer; and
(iii) directing incident radiation from a laser (e.g. a pulsed laser, such as an ultrafast laser) at the target layer to produce an ion-comprising plasma whereby ions from said plasma are implanted into the substrate.

The process may include controlling the implantation depth of ion implantation within the target layer by controlling any one of, or any combination of the following process parameters: the pulse repetition rate of the pulsed laser; the laser pulse energy: the duration of application of the process of implantation (e.g. the deposition time). The method may include selectively increasing (or decreasing) any one or more of these process parameters to increase (or decrease) the implantation depth. The process may include controlling the value of the refractive index of the ion-implanted region within the target layer by controlling any one of, or any combination of the following process parameters: the pulse repetition rate of the pulsed laser; the laser pulse energy; the duration of application of the process of implantation (e.g. the deposition time). The method may include selectively increasing (or decreasing) any one or more of these process parameters to increase (or decrease) the value of the refractive index of the ion-implanted region. Any variation/alteration in one such process parameter may be performed whilst holding one or all of the other process parameters substantially constant, or whilst also varying/altering one or all of the other process parameters.

The term 'about' when used in this specification refers to a tolerance of ±10%, of the stated value, i.e. about 50% encompasses any value in the range 45% to 55%, in further embodiments 'about' refers to a tolerance of ±5%, ±2%, ±1%, ±0.5%, ±0.2% or 0.1% of the stated value.

The term 'animal' includes mammals, such as humans.

The term 'dopants' refers to ions implanted into a substrate. Dopants include ions implanted into substrates of the invention.

The term 'glass' refers to a solid that possesses a non-crystalline (i.e., amorphous) structure and that exhibits a glass transition when heated towards the liquid state and which transmits light in the infrared, visible or ultraviolet spectrum, i.e. a wavelength of about 10 nm to 300 µm. In one embodiment 'glass' refers to a glass which transmits light in the visible spectrum i.e. a wavelength of about 380 nm to about 740 nm. In a further embodiment 'glass' refers to a glass which transmits light in the infrared spectrum i.e. a wavelength of about 740 nm to about 300 µm. In a further embodiment 'glass' refers to a glass which transmits light in the ultraviolet spectrum i.e. a wavelength of about 10 nm to about 380 nm. In a yet further embodiment 'glass' refers to a glass which transmits light in the wavelength range about 400 nm to about 2000 nm.

The term 'implantation' refers to ion entering the matrix of the substrate rather than forming a film on the surface of the substrate.

The term 'optical polymer' refers to any polymer which transmits light in the infrared, visible or ultraviolet spectrum, i.e. a wavelength of about 10 nm to 300 µm. In one embodiment 'optical polymer' refers to a polymer which transmits light in the visible spectrum i.e. a wavelength of about 380 nm to about 740 nm. In a further embodiment 'optical polymer' refers to a polymer which transmits light in the infrared spectrum i.e. a wavelength of about 740 nm to about 300 µm. In one embodiment 'optical polymer' refers to a polymer which transmits light in the ultraviolet spectrum i.e. a wavelength of about 10 nm to about 380 nm. In a yet further embodiment 'optical polymer' refers to optical polymers which transmits light in the wavelength range about 400 nM to about 2000 nm.

The term 'substrate' includes a reference to a silicon-based substrate or a polymeric substrate, for example, a material selected from glass or an optical polymer.

The term 'waveguide' refers to any element which facilitates transmission of light therethrough, such as guided transmission. The term includes a reference to any element which facilitates transmission of light into a material of interest and facilitates measurement of light which is retrieved from the material of interest.

The invention will now be illustrated with the following non-limiting examples with reference to the following figures.

BRIEF DESCRIPTION OF THE SEVERAL VIEWS OF THE DRAWING(S)

ABBREVIATIONS USED

HAADF high angle angular dark field elemental mapping
NIR near infra red
SEM Scanning electron microscopy
TEM Transmission electron microscopy

DETAILED DESCRIPTION OF THE INVENTION

Example—Implantation into Silica Glass

Figure 1:
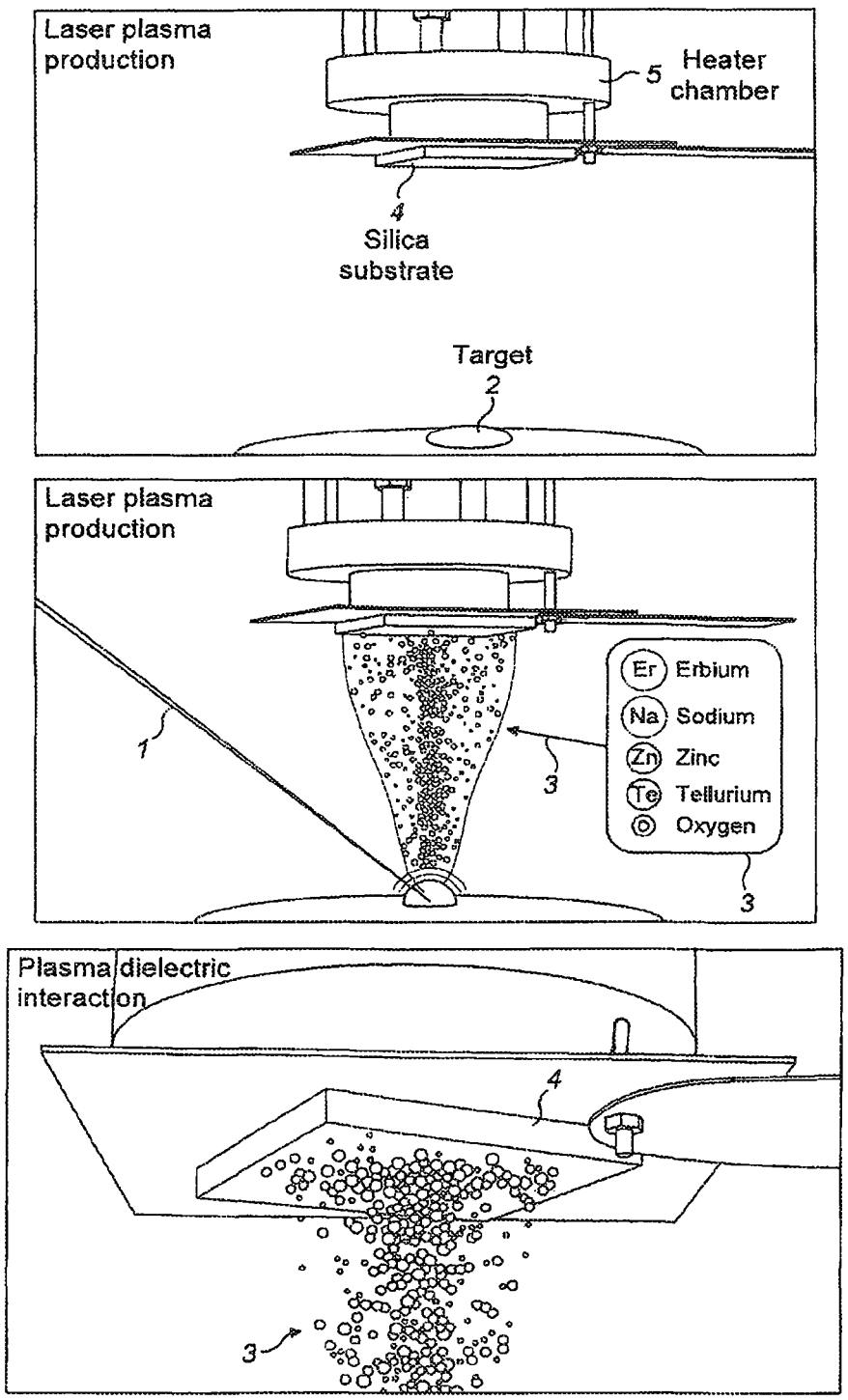
FIG. 1 shows schematically the ablation, plasma production and the multi-ion implantation process.

Multi-ion implantation into silica glass 4 was produced via femtosecond laser ablation of an erbium doped tellurite glass target containing zinc and sodium. A Ti-sapphire femtosecond laser 1 operating at a wavelength of 800 nm with 100 fs pulse width and a maximum repetition rate of 1 kHz (Coherent Inc, Santa Clara, Calif., U.S.A.) was used to ablate the glass target 2 generating an expanding plasma plume 3 consisting of multiple metal ions (multi-ion). A tellurite glass target with a molar composition of $79.5TeO_2$:$10ZnO$:$10Na_2O$:$0.5Er_2O_3$ produces multiple ions of Te, Zn, Na and Er, which diffuse into the silica glass substrate 4 under certain process conditions. The silica glass substrate was coupled to a heater chamber arranged to heat the substrate to a desired temperature. The ablation, plasma production and the multi-ion implantation process are schematically shown in FIG. 1.

Experiments were carried by varying the laser energy, repetition rate, target to substrate distance and finally the deposition target temperature. The deposition target was not translated for the simplicity of the experiment and for a better understanding of parameter variation along the sample surface. There was a variation in implantation depth and refractive index profile along the surface when radially moving outwards from the centre, therefore all the characteristic properties of the modification provided were measured from the centre of the sample unless otherwise stated.

Figure 2A:
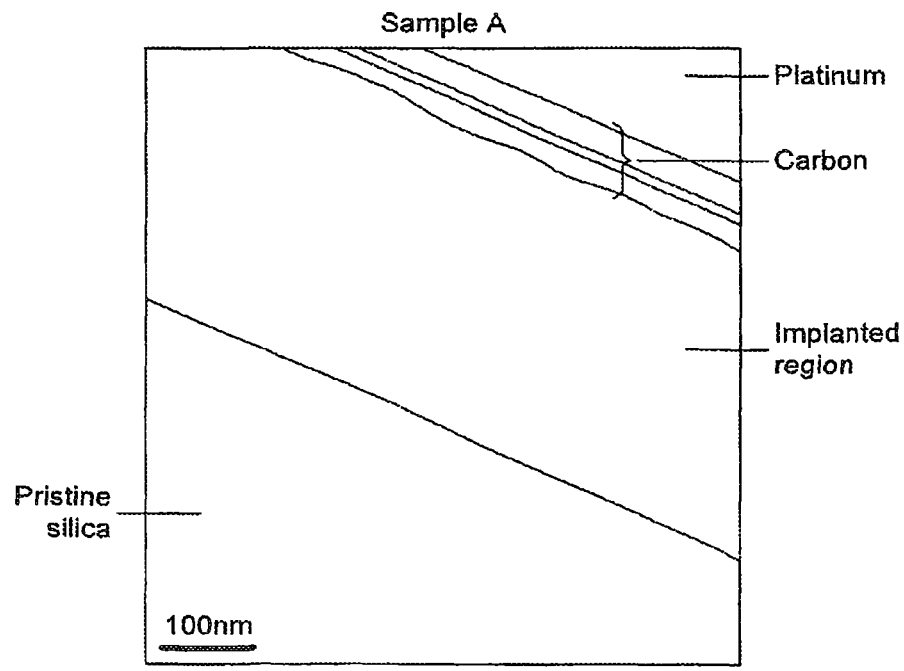
FIG. 2 shows the SEM and TEM images of the substrate cross sections with a highly defined and substantially uniformly implanted region in silica at two different target ablation energies of 47 µJ (Sample A) and 63 µJ (Sample B) respectively.
Figure 2B:
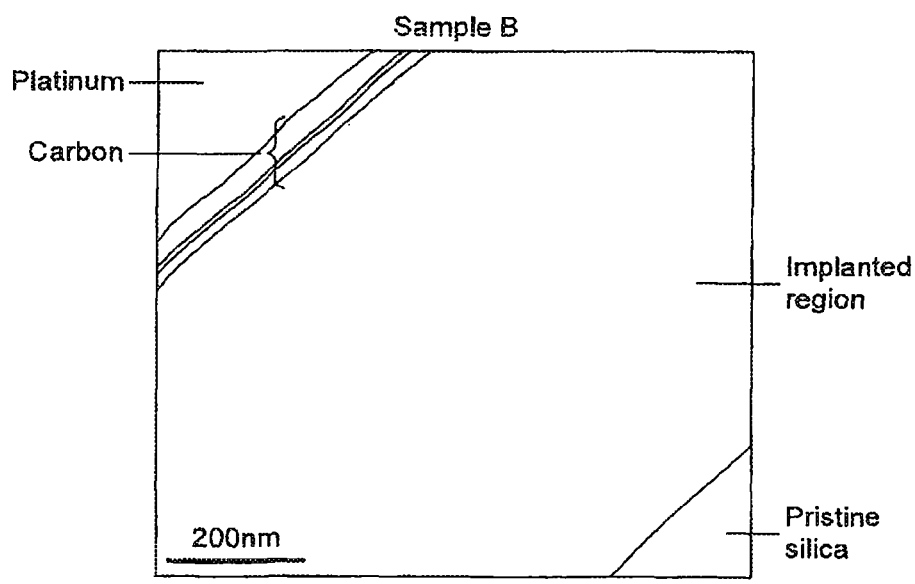

Optimum results were obtained for laser energies between 40 µJ-75 µJ when operated at 500 Hz and 1 kHz. The ablation target to substrate distance was set at 70 mm and the substrate temperature was set at 973K. FIG. 2 represents the SEM and TEM images of the substrate cross sections with a highly defined and substantially uniformly implanted region in silica at two different target ablation energies of 47 µJ (Sample A) and 63 µJ (Sample B) respectively. Diffusion depths of the ions increased from 350 nm to 850 nm with laser energy while the deposition time was 6 hours and repetition rate was 500 Hz for both cases. A well-defined boundary of the diffused and pristine region is clearly visible in the FIG. 2 and the modified region does not show any major clustering of ions or particle inhomogeneities.

Figure 3:
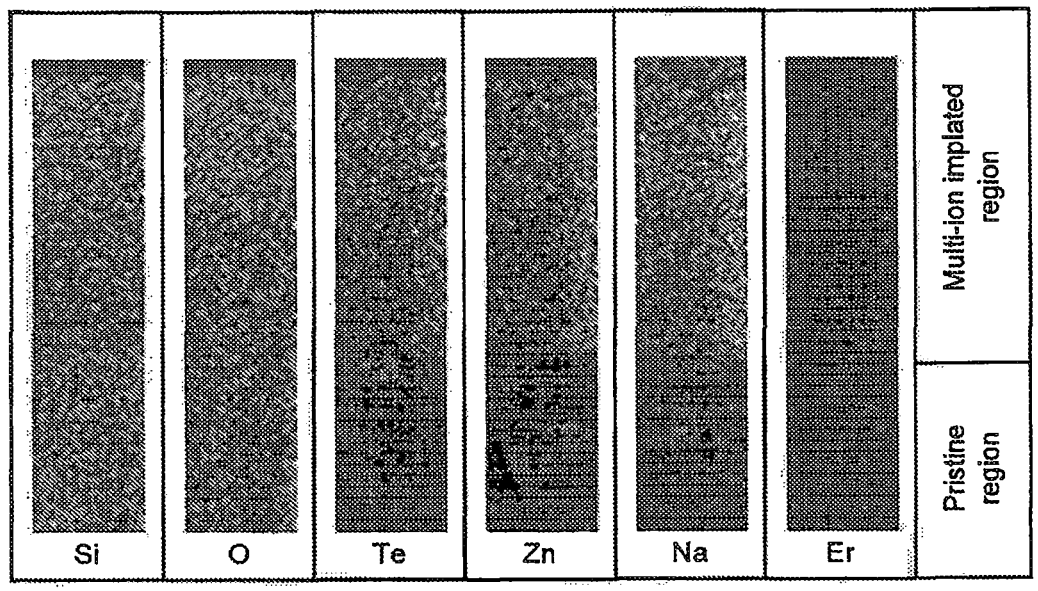
FIG. 3 shows a 400×1600 nm HAADF slices of individual elements of Sample B with line intensity profiles of the elements.
Figure 3:
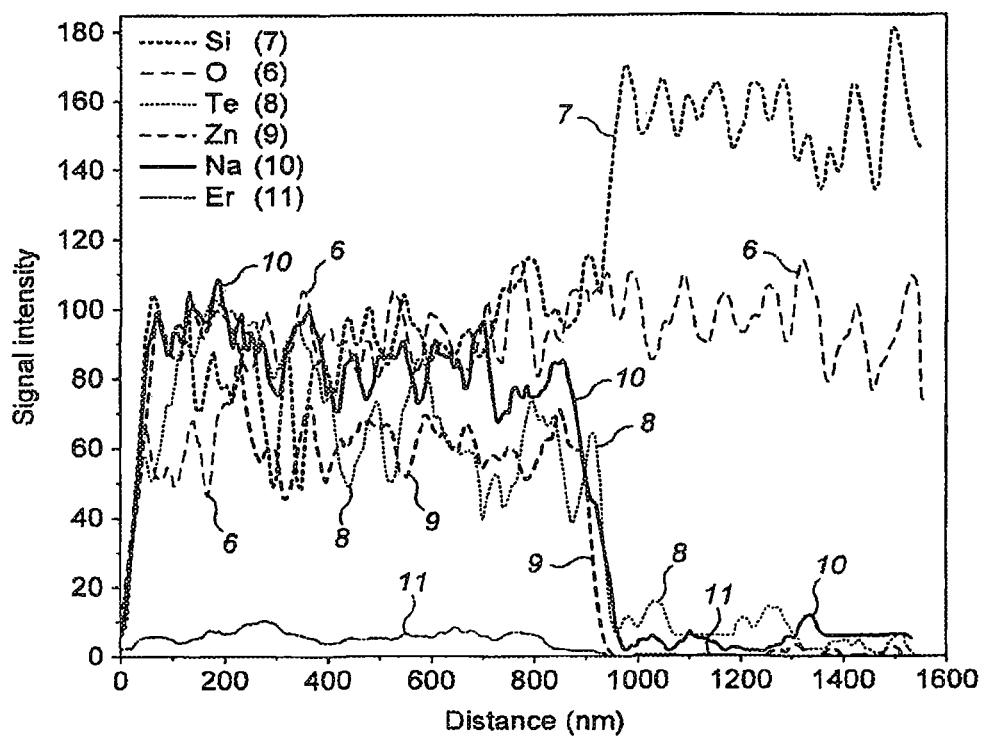

Further analysis of the diffusion characteristics of each ions in silica was carried out using high angle angular dark field (HAADF) elemental mapping of sample B. FIG. 3 depicts a 400×1600 nm HAADF slices of individual elements. A line intensity profile shows the relative concentration profile of each diffused elements with a well-defined and sharp boundary within the silica. The oxygen concentration 6 in silica remained unchanged across the boundary while silicon 7 showed a complementary concentration profile with respect to the diffused elements. This indicates the formation of a complex glass of silica with implanted ions increasing refractive index from 1.457 of that of silica to 1.626. Considering only the cations, the atomic concentration of silicon in the diffused region is determined to be 57% while Te (curve 8), Zn (curve 9), Na (curve 10) and Er (curve 11) constitute the rest in Sample A. This confirms a single step multi-ion implantation process in the silica glass substrate.

The implanted layer is highly substantially uniform and homogenous along the transverse and horizontal sections of the silica substrate. This could vary for silicon or other substrates and formations of crystallites and nano-crystallites are possible.

The process for making the ion-implanted substrate of the invention generally comprises ablating a target layer with incident radiation from a laser in the presence of a substrate whereby to implant a quantity of the target layer in the substrate. The target layer when exposed to incident laser radiation produces a plasma comprising ions capable of implanting into the substrate. The substrate is heated to facilitate the implantation of ions into the substrate. The substrate is spaced apart from the target layer e.g. at a distance of about 70 mm.

One or more masks or stencils may cover the surface of the substrate being implanted with the ions thereby to facilitate implantation of ions in specific zones of the substrate. These zones may form photonic circuits such as optical waveguide structures and pathways in the substrate, or other optical components/structures.

Figure 4:
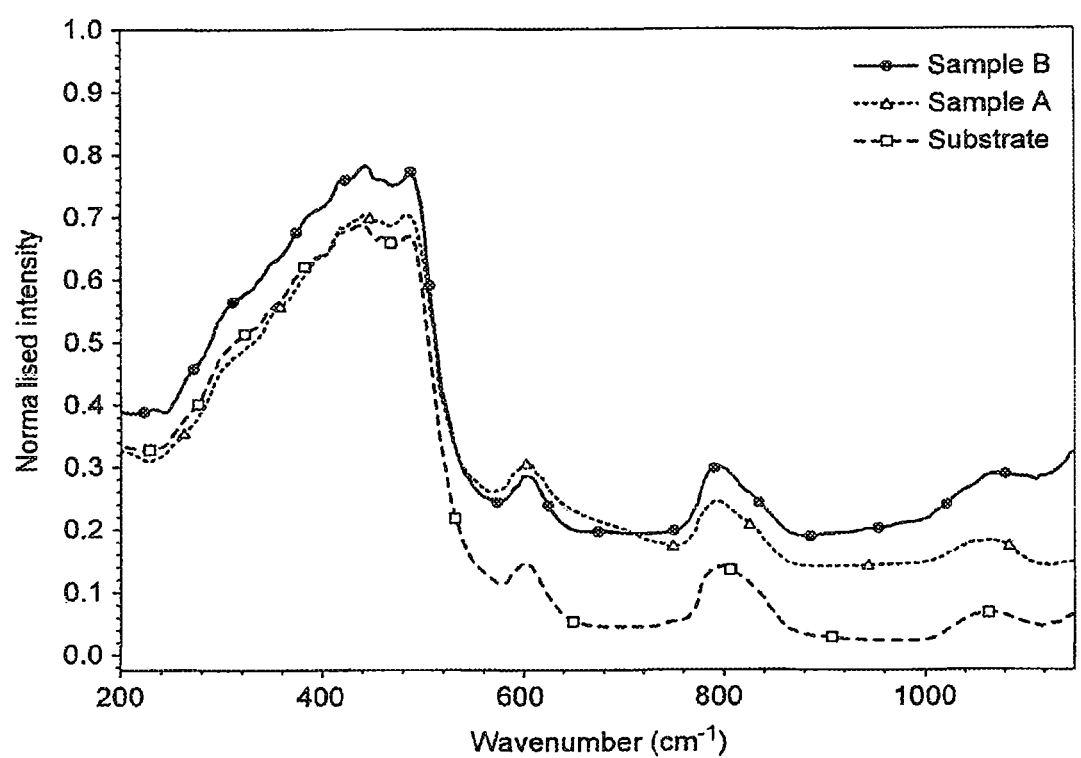
FIG. 4 represent the Raman spectrum of ion diffused glass compared with bare silica and tellurite bulk glass.

Structural Properties of Implanted Region:

Silica and tellurite are completely immiscible and will not form a stable glass under conventional batch melting and quenching process. However in the results presented above it is demonstrated that diffusion of metal cations including $Te^{4+}$ ions in to the silica glass network is possible with network modification. The properties of the implanted silica glass were measured. No signals of any kind of crystallization were observed in electron diffraction and XRD characterization proving a complete amorphous phase of silica-tellurite glass. Raman spectroscopy was used to analyse the glass network in the diffused region. FIG. 4 represent the Raman spectrum of ion diffused glass compared with bare silica and tellurite bulk glass which is devoid of any characteristic signals corresponding to $TeO_2$ glass phase within the network.

Figure 5A:
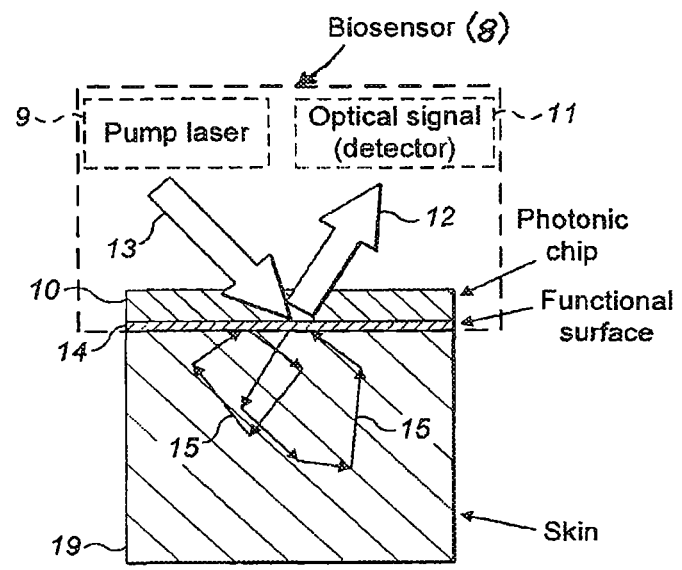
FIG. 5A represents a schematic diagram of a biosensor, such as a glucose sensor of the invention.
Figure 5B:
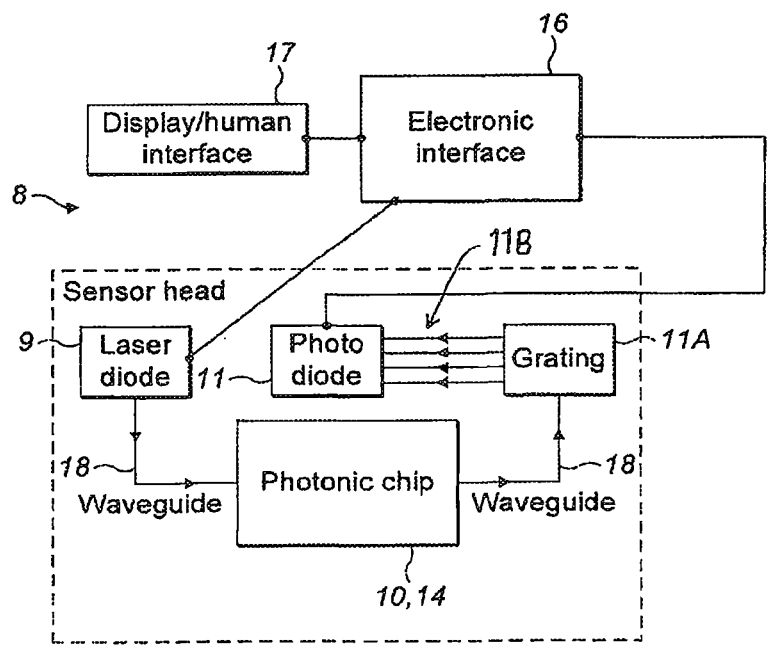
FIG. 5B represents a schematic diagram of the biosensor of FIG. 5A.

FIGS. 5A and 5B represents a schematic diagram of a biosensor 8 of the invention for use as a glucose sensor. The biosensor comprises a pump laser 9, an ion-implanted substrate of glass 10, and a light detector 11 for detecting optical signals 12 emanating from the ion-implanted substrate. The pump laser is arranged to emit laser light 13 having a suitable wavelength for causing implanted ions 14 within the substrate to fluoresce. The light detector is a fast photodiode, such as a microsecond photodiode, or a nanosecond photodiode and is arranged to detect the intensity of fluorescence of the implanted ions within the substrate. That is to say, the photodiode preferably has a response time whereby an electrical detection signal is generated within microseconds, or more preferably nanoseconds in response to the presence of light at the detector, and that such electrical signal stops within the same or similar rapid time period after light is no longer present at the detector. This speed is preferable in order to allow the apparatus to have a desired degree of temporal resolution permitting separate, brief fluorescence detections in rapid succession. A similarly rapid photomultiplier device may be used as an alternative.

The substrate has a substantially uniform thickness which is in the range of about 0.1 mm to about 10 mm, such as in the range of 0.5 mm to about 3 mm. The ion implanted substrate defines at its implanted surface region 14 a functional surface for the optical detection of the presence of glucose via photons of fluorescent light 15 generated in the implanted region of the substrate. It may be referred to as a photonic chip. Indeed, a substrate of the invention may be formed directly upon the surface of a laser such as a solid-state laser whereby the functional surface of the substrate is pumped by the solid-state laser in use. This offers a very compact photonic chip design.

The biosensor includes not only the light detector but also a data processor unit 16 connected to the light detector for receiving light detection signals from the light detector and for generating data representing those detections. The biosensor further includes a control unit 17 comprising software, or firmware or electronic circuitry, arranged for controlling the operation of the pump laser and/or the light detector and/or the data processor unit as desired. The combination of the light detector and the data processor unit may be referred to as a photonic chip integrator, in its relationship to the photonic chip. The control unit may output detected signals, received from the signal processor unit, to display at a display of human interface of the control unit 17. Optical waveguides (18) guide pump light from the pump laser 9 to the substrate 10, and guide fluorescent light from the substrate to the photodiode via a diffraction grating 11A arranged to separate the received fluorescent light into desired spectral wavelength bands for output to the optical detector on a dedicated spectral channel 11B (e.g. a waveguide). This allows the photodiode to detect selected spectral channels independently; e.g. by blocking receipt of light of all but the channel(s) it is desired to detect.

The ion-implanted layer of the substrate is formed to extend into the body of the substrate from a planar surface/face of the substrate to a substantially uniform depth of at least 50 nm (e.g. at least 200 nm) into the glass and has a substantially uniform distribution of implanted ions throughout that depth. The implanted layer also extends across the planar surface to provide a functional surface area of sensitivity for glucose detection. The surface are may be several square mm, or square cm, in size. The distribution of implanted ions throughout that area is also substantially uniform. The pump laser and light detector are both optically coupled to a rear surface area of the substrate which is the reverse surface to functional surface area. This means that the functional surface area may be applied or located at a desired object or target of study (e.g. the skin or an animal, 19), while the pumping of the functional area and the subsequent detection of light emanating from the functional surface area may take place away from the target without requiring the functional surface to be moved relative to the target. This permits compactness in the biosensor, and ease of use.

This use of ion-implanted substrates of the invention permits non-invasive detection of metabolites, such as glucose, in animals. The detection method is a novel method which measures a photoluminescence lifetime to detect metabolites such as glucose, rather than simply detecting from an isolated light intensity measurement.

Figure 6:
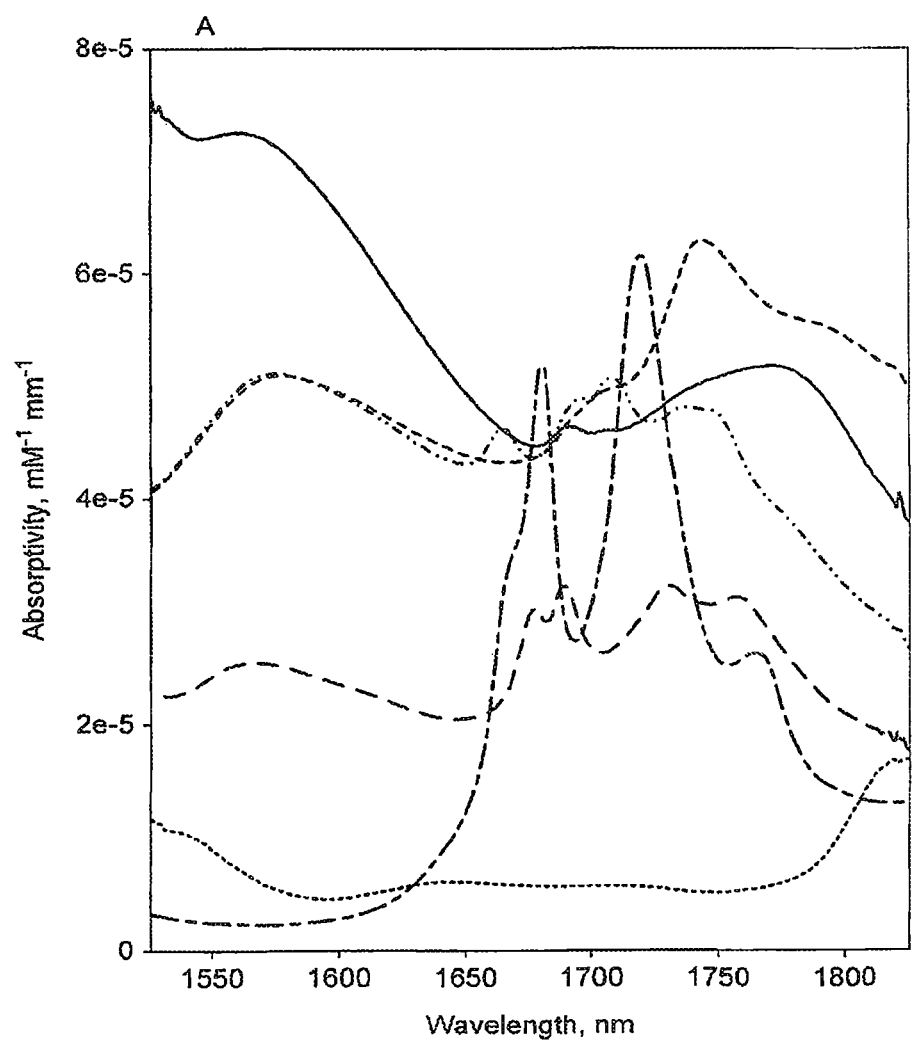
FIG. 6 shows Molar absorptivity spectra of glucose (solid), alanine (dashdot-dot), ascorbate (medium dash), lactate (short dash), urea (dotted), and triacetin (dash-dot) at 37.0±0.1° C. over the first overtone.

The photoluminescence spectral band of the dopant(s) within the ion-implanted substrate overlaps with the characteristic absorption bands (e.g. in the range 1530-2200 nm) of glucose molecules in the near-infrared (NIR) wavelengths. An example of these absorption bands is illustrated in FIG. 6 for Glucose and for other molecules (see Airat K. Amerov et al., Appl. Spectrosc. 58 (10), 1195 (2004)).

In particular, FIG. 6 shows the Molar absorptivity spectra of glucose (solid line), alanine (dashdot-dot line), ascorbate (medium dash line), lactate (short dash line), urea (dotted line), and triacetin (dash-dot line) at 37.0±0.1° C. over the first overtone. Thus, while the present embodiment is described in terms of glucose detection, it will be readily appreciated that it may be applied to detection of other molecules such as those described above.

By measuring/detecting fluorescence lifetimes at selected wavelengths of light falling within regions of the absorption spectrum of a metabolite in which significant spectral variations occur, such as sharp, or sustained changes in absorption levels, one may identify the presence of that metabolite in terms of the corresponding changes in the measured fluorescence lifetimes at different optical wavelengths within that regions of the absorption spectrum of a metabolite. For example, Glucose has a strong spectral slope in the wavelength region of about 1525 nm to about 1650 nm as shown in FIG. 6, whereas the other metabolites represented in FIG. 6 have far less spectral variation there. This means that detected spectral variations in detected fluorescence lifetimes within that spectral region and can be used to infer or confirm the presence of Glucose. This applies similarly to other metabolites at other spectral regions.

Figure 7:
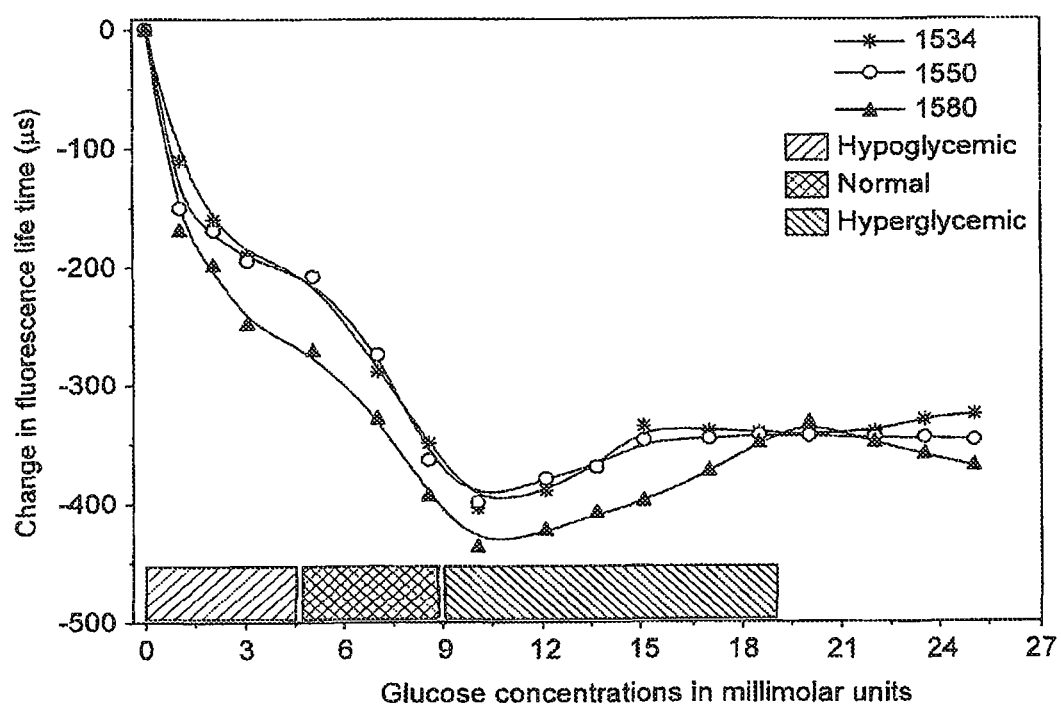
FIG. 7 shows the variation in photoluminescence lifetime measured at three different wavelengths (1543 nm, 1550 nm, 1580 nm) for human blood sample with varying concentrations of glucose.
Figure 8:
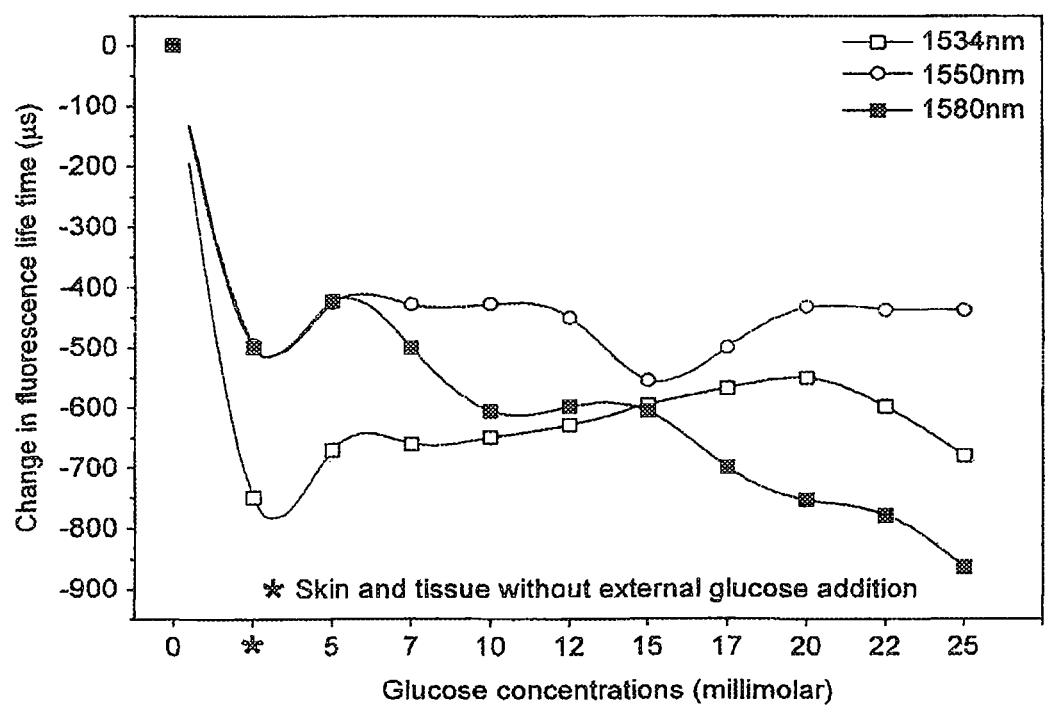
FIG. 8 shows the non-invasive measurement of glucose carried out on porcine skin.

FIG. 7 and FIG. 8 show detected changes in fluorescence lifetimes when the biosensor is applied (in the manner shown in FIG. 5 or FIG. 11) to a blood sample containing Glucose (FIG. 7) or a sample of porcine skin (FIG. 8). It can be seen that at longer wavelengths (1580 nm) the change in fluorescence lifetime is the greatest and can be more sustained in its correlation with Glucose concentrations (see FIG. 8). In this regard, the biosensor may be arranged to operate at one particular wavelength (e.g. 1580 nm) selected from amongst a plurality of wavelengths, which provides such a favourable response or sustained correlation.

The measured photoluminescence lifetime of the rare earth implanted ions becomes modified within the glass thin film contained in a photonic sensor due to the amplification by random scattering and localization of photoluminescent photons. When a target medium containing glucose (e.g. skin) interacts with fluorescent photons from the ion-implanted film, via the ion-implanted functional surface, the apparent photoluminescence lifetime becomes modified as a function of glucose concentration within the target medium due to its specific absorption as well as molecular scattering properties.

Thus by an accurate measurement of the photoluminescence lifetime of the rare earth implanted ions in the functional surface, the concentration of glucose in the medium can be deduced. Since the absorption and scattering properties of the photons at different wavelengths within the emission band varies as a function of glucose concentration, the apparent change in the photoluminescence lifetime of the rare earth implanted ions at different wavelengths can be used as an additional feature to enhance the signal due to glucose as compared to that from other interferences (e.g. metabolites) as described above with reference to FIG. 6. This new measurement concept may be referred to as the Spectrally Resolved Photoluminescence Lifetime (SRPL) technique and is the novel principle of detection that may be applied in the biosensor.

The method for the non-invasive measurement of a metabolite using the biosensor includes:
   applying the biosensor on or near the subject being sensed, such as applying the functional surface of the biosensor to the skin of an animal;
   irradiating the functional surface with pump light from the pump laser for a pumping period of time to excite fluorescence in the functional surface, and such that a portion of the fluorescent light escapes into the animal;
   measuring the photoluminescence lifetime of fluorescent light from the functional surface, after the pumping period has ended, using the photodiode and the signal processor unit.

The signal processor unit is arranged to determine the time period (the "recovery lifetime") required for the measured intensity of fluorescence light to fall in value by a factor of 1/e. This period preferably begins immediately from the ending of the pumping period such that no pumping of the functional surface takes place during the lifetime measurement period. The measured recovery lifetime of detected fluorescent light from the functional surface is correlated with the level of the metabolite within the subject being sensed as described above. The signal processor is arranged to calculate a value of the metabotite (e.g. Glucose) concentration level using such pre-determined correlations. These pre-determined correlations for a given metabolite such as Glucose (i.e. concentration levels corresponding to measured recovery lifetime) may be pre-stored in a look-up table within the signal processor unit (or in a separate memory accessible by the signal processor unit) from which the signal processor unit determines a concentration level from a given measured recovery lifetime and outputs the result either for display to a user or for storage as desired.

Figure 10:
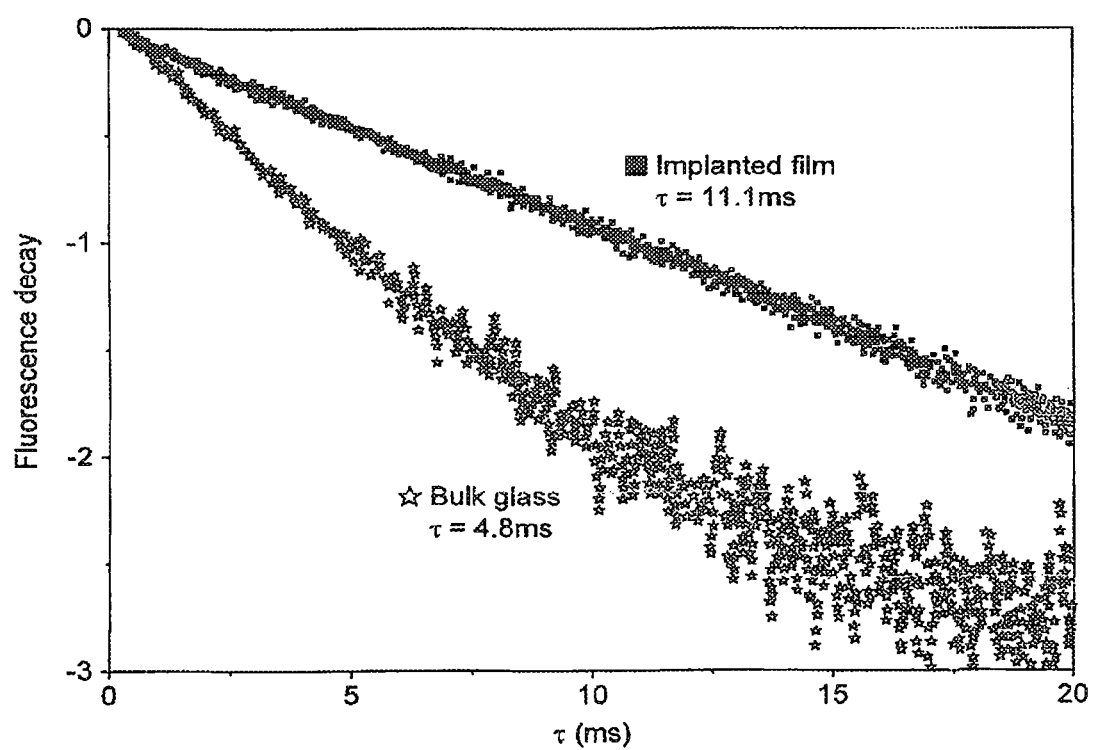
FIG. 10 shows the photoluminescence lifetime at a wavelength of 1535 nm, of sample B compared with the target glass used to prepare sample B (i.e. the ablated target glass).
Figure 11:
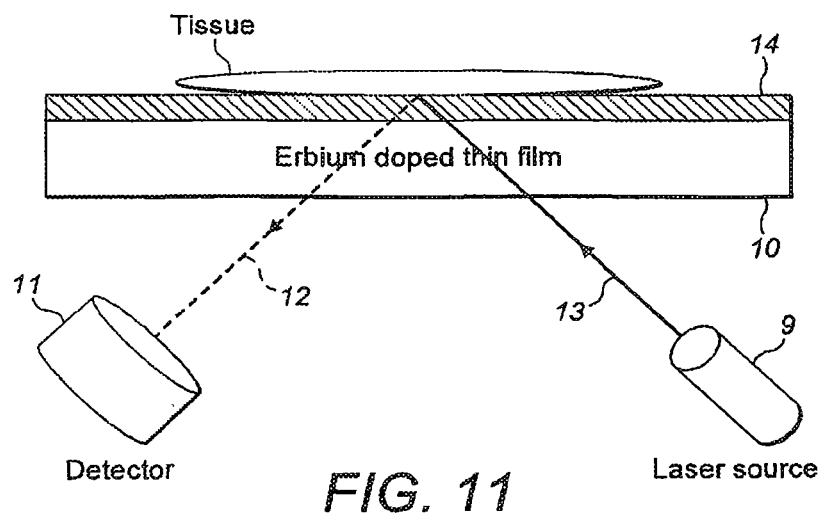
FIG. 11 represents a schematic diagram of a biosensor, such as a glucose sensor of the invention.

The control unit 17 is arranged to control the pump laser to resume pumping the functional surface with pump light after a defined period of time exceeding the recovery lifetime. This controlled on/off switching of the pump laser may occur at a repetition rate to suit the user. The "on" period permits the pump laser to pump the implanted ions of the functional surface, while a successive "off" period permits a recovery lifetime to be measured, and a metabolite concentration to be determined. FIG. 10 illustrates the decay in detected fluorescence light levels in the functional surface when isolated from any measurement subject. The exponential decay falls by a factor of 1/e after 11.1 ms which corresponds to the recovery lifetime of the functional surface in isolation. This recovery lifetime is changed in the presence of a metabolite such as Glucose, and the amount of change is correlated to the amount of glucose. FIG. 7 shows an example correlation when the subject being measured is a free blood sample containing Glucose (in vitro) as shown in FIG. 11, whereas the correlation shown in FIG. 8 is obtained from a porcine skin sample as shown in FIG. 5. FIG. 10 also shows a decay curve for the target glass used to generate the plasma cloud (FIG. 1) during ion implantation of the substrate.

Figure 12:
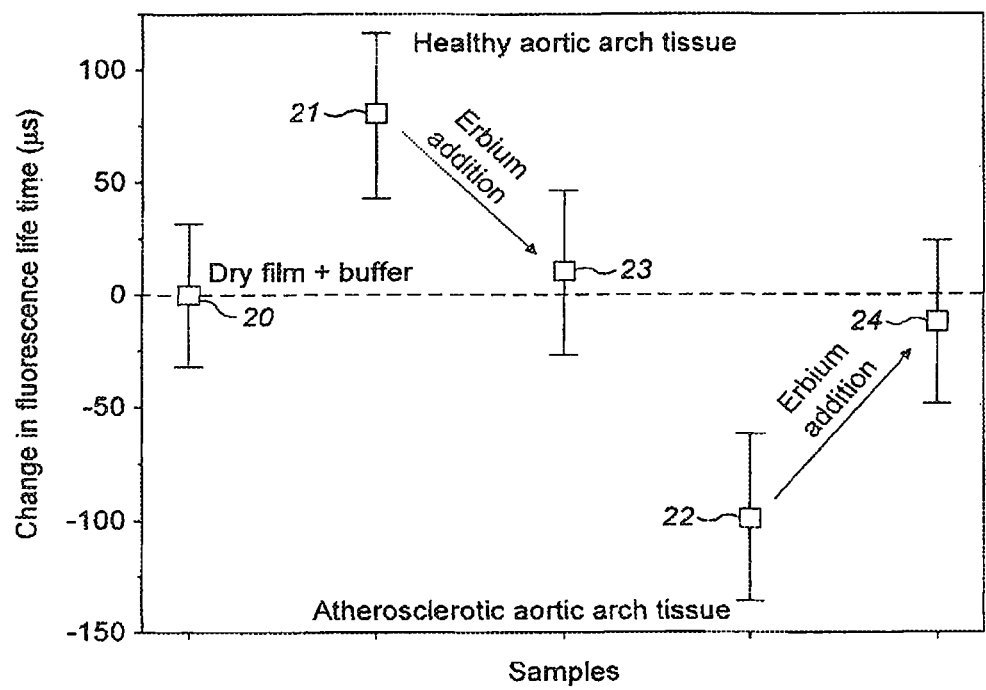
FIG. 12 shows measurement results for detection of healthy and unhealthy aortic arch tissue.

FIG. 12 illustrates the ability of the biosensor to distinguish between normal aortic tissue and abnormal aortic tissue, such as atherosclerotic tissue. This illustrates the use of the biosensor for sensing cardio-vascular disease and cancers. The change in fluorescence lifetime is shown in FIG. 12 for five different circumstances. The leftmost data point 20 in the figure corresponds to a circumstance where the biosensor is not in contact with any subject tissue. The change in fluorescence lifetime is zero. The next data point 21 corresponds to healthy aortic tissue and shows a positive change in fluorescence lifetime, whereas a negative change 22 in fluorescence lifetime is seen for atherosclerotic tissue. This illustrates a measurement method for determining the presence of healthy or unhealthy tissues as follows.

First, the fluorescence lifetime of the functional surface of the biosensor is determined in the absence of tissue; next, the tissue is applied to the functional surface of the biosensor and a new fluorescence lifetime is determined in the presence of the tissue (e.g. in vitro as in FIG. 11). If the latter fluorescence lifetime is greater than the former, then the tissue is healthy, else it is unhealthy if the latter fluorescence lifetime is less than the former. The signal processor of the biosensor may be arranged to make this determination.

In a further enhancement of this method, Erbium (e.g. in a salt solution: e.g. Erbium Chloride) may be added to the tissue, and a second fluorescence lifetime measured. If the second fluorescence lifetime 23 is less than the first-measured fluorescence lifetime (for the Erbium-free tissue) then this is indicative of healthy tissue, otherwise if the second fluorescence lifetime 24 is greater than (i.e. less negative) the first-measured fluorescence lifetime (for the Erbium-free tissue) then this is indicative of unhealthy tissue. The signal processor of the biosensor may be arranged to make this determination.

The substrate of the biosensor, and in other aspects of the invention, is provided with an ion-implanted layer in which the ion implanted layer extends substantially from the outermost surface of the substrate. This is shown in FIG. 3 which shows the concentration of dopant ions, and of substrate glass as a function of depth into the substrate from the outermost surface of the glass through which implantation took place. The left-hand part of FIG. 3 shows a HAADF slices as described above indicating concentrations of dopants and other atoms of the substrate. It is to be noted that the line trace graphs of the HAADF slices shown to the right of FIG. 3 begins just above the outermost surface of the glass, which surface is indicated by the initial sharp rise in HAADF signal intensities at a "distance" on the graph of a few nm. The ion-implanted layer has a substantially uniform distribution of the implanted ions extending into the substrate from its outermost surface.

Figure 9:
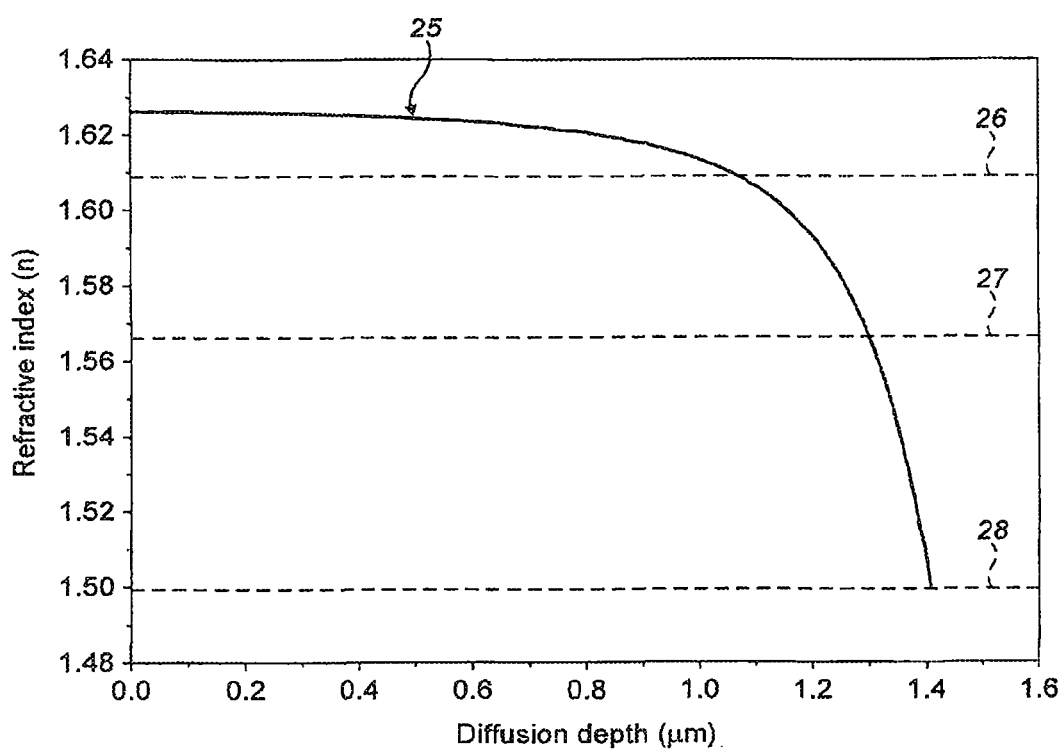
FIG. 9 shows the refractive index profile of sample B.

This ion distribution produces a region of substantially uniformly increased refractive index in the substrate as is indicated by the approximate (simulated) effective refractive index profile 25 shown in FIG. 9. This profile illustrates an approximate representation of the change in refractive index of the substrate with increasing depth from the surface of the ion-implanted layer. The continuous curve represents a simulation (approximate) of the effective refractive index distribution based on the measured optical properties (e.g. refractive indices) of three different optical propagation modes (26, 27, 28) measured within the substrate, and calculated according to standard techniques for determining effective refractive indices using optical propagation modes as would be readily apparent to the skilled person. The result is a substantially uniform refractive index of about 1.625 (measured at a wavelength of 633 nm, using a He Ne laser) across the implanted layer, falling as rapidly to the refractive index of the substrate glass at a depth of about 1.4 microns where the implanted layer ends. The refractive index distribution is a "step index" distribution and results from the uniformity of the ion distribution within the substrate. A more accurate simulation would show a sharper step change in refractive index at a depth of 1.4 microns. Note that the refractive index of the substrate material was about 1.457 whereas the refractive index of the implanted layer is 1.625—a very significant increase.

Figure 13:
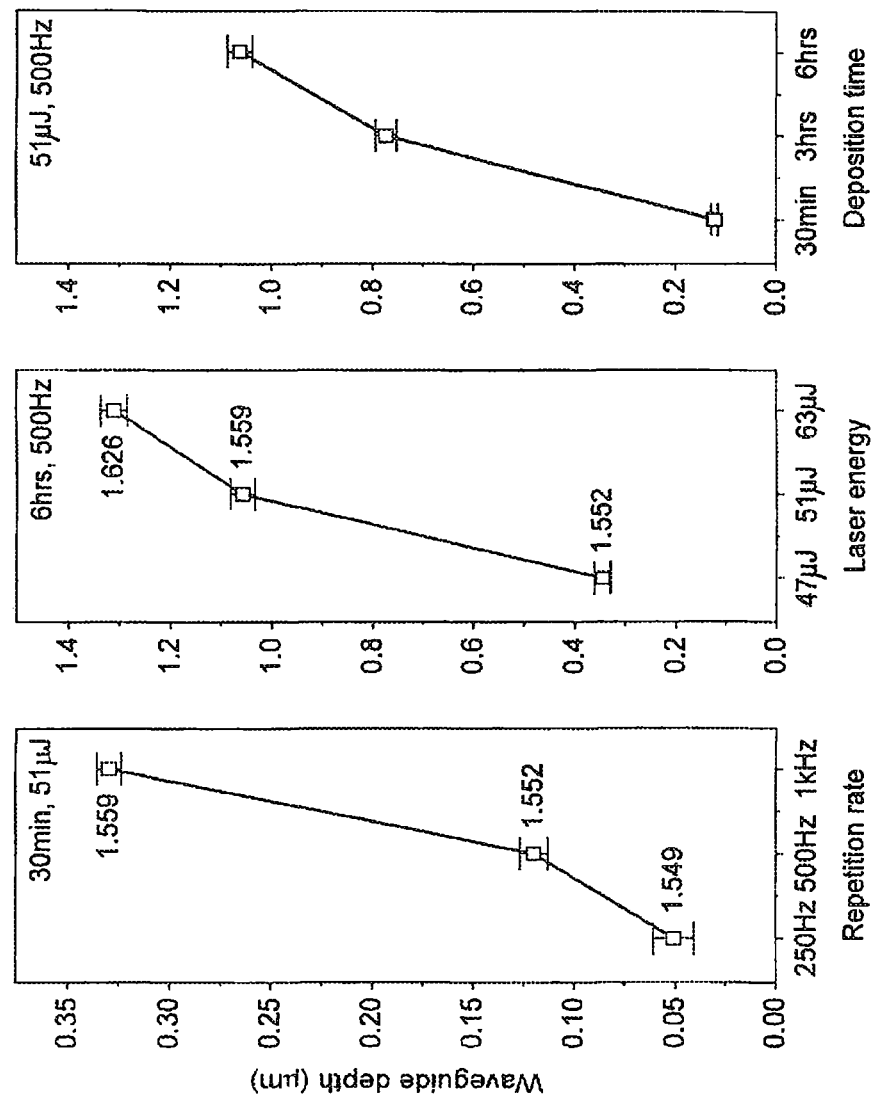
FIG. 13 shows the variation in implanted ion layer depth/thickness (measured from the surface of a substrate e.g. "waveguide" containing the implanted layer) as a function of the parameters of the pulsed laser light employed to ablate a target glass to produce an ion cloud for implantation.

FIG. 13 shows the variation in implanted ion layer depth/thickness measured from the surface of a substrate (e.g. "waveguide") containing the implanted layer, as a function of the parameters of the pulsed laser light employed to ablate a target glass to produce and ion cloud for implantation. It can be seen that the depth (layer thickness) as well as the refractive index of the layer, increase with pulse repetition rate and laser pulse energy in the ablating laser. Increasing the layer deposition time also increases the layer thickness/depth.

The left graph of FIG. 13 shows the implanted layer depth and refractive index (the four-digit numbers adjacent to data points) as a function of increasing pulse repetition rate. The deposition time was 30 minutes at 51 microjoules per pulse of ablating laser light. The middle graph of FIG. 13 shows the implanted layer depth and refractive index (the four-digit numbers adjacent to data points) as a function of increasing pulse energy. The deposition time was 6 hours at a pulse repetition rate of 500 Hz. The right graph of FIG. 13 shows the implanted layer as a function of increasing deposition time. The pulse repetition rate was 500 Hz at 51 microjoules per pulse of ablating laser light.

The invention claimed is:

1. A process for fabricating an ion-implanted layer in a substrate comprising silicate glass, the process comprising:
    providing a target layer comprising a tellurite glass in a vacuum chamber at a reduced pressure;
    providing said substrate in the vacuum chamber which includes a surface of the substrate in proximity to said target layer wherein the surface of the substrate is spaced from the target layer by a distance in the range 50 mm to 70 mm;
    heating the substrate to a temperature in the range from $0.55\ T_g$ to $0.75\ T_g$ where $T_g$ is the glass transition temperature of the substrate; and,
    directing pulses of incident radiation from a laser at the target layer thereby ablating material of the target layer with said incident radiation to produce therefrom a plume of the ablated target material capable of implanting into the heated substrate with the target layer and the substrate in oxygen gas at said reduced pressure within the range 80 mTorr to 90 mTorr, whereby said ablated material of said plume is implanted into the heated substrate by entering the heated substrate via the surface of the heated substrate such that a film of said ablated target material is not formed on the surface of the heated substrate, thereby forming a layer of implanted ions of said ablated target material within the heated substrate which extends from the surface of the heated substrate to a depth of at least 50 nm and which has a density of said implanted ions of said ablated target material of at least $10^{21}$ ions $cm^{-3}$.

2. A process according to claim 1 wherein the laser is a Femtosecond laser.

3. A process according to claim 1 wherein said implanted ions of said layer of implanted ablated target material are arranged in a spatial distribution which is substantially uniform along a direction extending into the heated substrate from the surface of the heated substrate.

4. A process according to claim 1 wherein said layer of implanted ablated target material has a density of said implanted ions of at least $10^{23}$ ions cm$^{-3}$.

5. A process according to claim 1 in which the depth of the implanted ions of said layer of implanted ablated target material is at least 200 nm.

6. A process according to claim 1 where the depth of the implanted ions of said layer of implanted ablated target material is at least 500 nm.

7. A process according to claim 1 wherein said implanted ions of said layer of implanted ablated target material are arranged in a spatial distribution which is substantially uniform along a direction extending into the heated substrate.

8. A process according to claim 1 wherein the layer of implanted ablated target material either:
   (i) encompasses substantially the whole area of said surface of the heated substrate; or
   (ii) comprises one or more zones of said surface of the heated substrate.

9. A process according to claim 1 wherein the layer of implanted ablated target material comprises one or more zones of said surface of the heated substrate wherein the zones comprise the same or different ions.

10. A process according to claim 1 wherein the implanted ions are cations.

* * * * *